（12） United States Patent
Fujimori

(10) Patent No.: US 10,542,874 B2
(45) Date of Patent: Jan. 28, 2020

(54) IMAGING DEVICE AND ENDOSCOPE DEVICE

(71) Applicant: OLYMPUS CORPORATION, Tokyo (JP)

(72) Inventor: Noriyuki Fujimori, Suwa (JP)

(73) Assignee: OLYMPUS CORPORATION, Tokyo (JP)

( * ) Notice: Subject to any disclaimer, the term of this patent is extended or adjusted under 35 U.S.C. 154(b) by 514 days.

(21) Appl. No.: 15/227,352

(22) Filed: Aug. 3, 2016

(65) Prior Publication Data

US 2016/0338574 A1  Nov. 24, 2016

Related U.S. Application Data

(63) Continuation of application No. PCT/JP2015/054841, filed on Feb. 20, 2015.

(30) Foreign Application Priority Data

Mar. 3, 2014  (JP) .................................. 2014-041041

(51) Int. Cl.
*A61B 1/00* (2006.01)
*A61B 1/05* (2006.01)
(Continued)

(52) U.S. Cl.
CPC ...... *A61B 1/00163* (2013.01); *A61B 1/00096* (2013.01); *A61B 1/05* (2013.01);
(Continued)

(58) Field of Classification Search
CPC ....... A61B 1/05; A61B 1/051; A61B 1/00096; A61B 1/0011; H04N 2005/2255; H04N 5/2254; H04N 5/225; H04N 5/2251; H04N 5/2252; H04N 5/2257; G02B 23/2484; G02B 23/243; G02B 13/0015
(Continued)

(56) References Cited

U.S. PATENT DOCUMENTS 4,682,219 A  7/1987  Arakawa
2003/0149339 A1*  8/2003  Ishibiki .............. A61B 1/00096
                                                    600/160
(Continued)

FOREIGN PATENT DOCUMENTS

JP  S62-35314 U  3/1987
JP  H03-20312 U  2/1991
(Continued)

OTHER PUBLICATIONS

International Search Report dated May 19, 2015 issued in PCT/JP2015/054841.

*Primary Examiner* — Alexandra L Newton
(74) *Attorney, Agent, or Firm* — Scully, Scott, Murphy & Presser, P.C.

(57) ABSTRACT

An imaging device includes a lens group configured to collect incident light, a prism configured to reflect the light collected by the lens group, and an image sensor having a light receiving unit configured to receive the light reflected by the prism and to perform photoelectric conversion on the received light to generate an electrical signal. The prism is mounted on the light receiving unit, and the lens group is directly mounted on a surface of the image sensor.

11 Claims, 7 Drawing Sheets

(51) Int. Cl.
*G02B 23/02* (2006.01)
*G02B 23/24* (2006.01)
*H04N 5/225* (2006.01)

(52) U.S. Cl.
CPC .......... *G02B 23/02* (2013.01); *G02B 23/243* (2013.01); *H04N 5/2256* (2013.01); *H04N 2005/2255* (2013.01)

(58) Field of Classification Search
USPC ....................................................... 600/129
See application file for complete search history.

(56) References Cited

U.S. PATENT DOCUMENTS

| | | | |
|---|---|---|---|
| 2010/0085466 A1* | 4/2010 | Fujimori | A61B 1/00096 348/340 |
| 2012/0197081 A1* | 8/2012 | Kimura | A61B 1/00124 600/110 |
| 2012/0226102 A1* | 9/2012 | Kagaya | A61B 1/045 600/109 |
| 2014/0078280 A1* | 3/2014 | Yoshida | A61B 1/00163 348/76 |
| 2016/0213236 A1* | 7/2016 | Hruska | A61B 1/267 |

FOREIGN PATENT DOCUMENTS

| | | | | |
|---|---|---|---|---|
| JP | 2000-271066 A | | 10/2000 | |
| JP | 2002-45333 A | | 2/2002 | |
| JP | 2009-268639 A | | 11/2009 | |
| JP | 2012254176 A | * | 12/2012 | ......... A61B 1/00163 |

* cited by examiner

IMAGING DEVICE AND ENDOSCOPE DEVICE

CROSS REFERENCES TO RELATED APPLICATIONS

This application is a continuation of PCT international application Ser. No. PCT/JP2015/054841, filed on Feb. 20, 2015 which designates the United States, incorporated herein by reference, and which claims the benefit of priority from Japanese Patent Application No. 2014-041041, filed on Mar. 3, 2014, incorporated herein by reference.

BACKGROUND

1. Technical Field

The disclosure relates to an imaging device that is provided at a distal end of an insertion portion of an endoscope configured to be inserted into a subject to image a region to be examined, and relates to an endoscope device using the imaging device.

2. Related Art

Conventionally, in the medical field and the industrial field, endoscope devices are widely used for various examinations. Among these endoscope devices, a medical endoscope device can observe a region to be examined by inserting an elongate insertion portion having flexibility, which includes an imaging device at its distal end, into a body cavity of a subject such as a patient. However, the insertion portion is desired to be small in diameter so as to be easily introduced into the subject.

In general, an imaging device used for an endoscope or the like holds an outer circumference portion of a lens group of an objective optical system by a metallic frame member and defines a position of the lens group in a radial direction and an optical axis direction. However, an endoscope imaging device is disclosed in which as a technique to cause the insertion portion to be small in diameter, the height dimension is reduced by providing a gap in an optical path direction in a member that holds the frame member of the objective optical system and an outer circumferential surface of the gap portion is cut and thereafter the objective optical system is closely arranged to an upper surface of a solid state image sensor (for example, see JP 2000-271066 A and JP 2002-45333 A).

SUMMARY

In some embodiments, an imaging device includes: a lens group configured to collect incident light; a prism configured to reflect the light collected by the lens group; and an image sensor having a light receiving unit configured to receive the light reflected by the prism and to perform photoelectric conversion on the received light to generate an electrical signal. The prism is mounted on the light receiving unit, and the lens group is directly mounted on a surface of the image sensor.

In some embodiments, an endoscope device is configured to be inserted into a living body and includes the imaging device according to the above-mentioned invention to image an inside of the living body.

In some embodiments, an endoscope device includes an insertion portion configured to be inserted into a living body to acquire in-vivo information, the insertion portion including an imaging device in a distal end portion of the insertion portion. The imaging device includes: a lens group configured to collect incident light; a prism configured to reflect the light collected by the lens group; and an image sensor including a light receiving unit configured to receive the light reflected by the prism and to perform photoelectric conversion on the received light to generate an electrical signal. The image sensor is supported by a component of the distal end portion.

The above and other features, advantages and technical and industrial significance of this invention will be better understood by reading the following detailed description of presently preferred embodiments of the invention, when considered in connection with the accompanying drawings.

DETAILED DESCRIPTION

Reference will be made below to an endoscope device having an imaging module as modes for carrying out the present invention (hereinafter referred to as an "embodiment(s)"). The present invention is not limited by the embodiments. The same reference signs are used to designate the same elements throughout the drawings. Further, the drawings are schematic, and it is noted that the relation between the thickness and the width of each member and the ratio of the size of each member are different from the reality. The size and the ratio of the same elements may be different in a different drawing.

Figure 1:
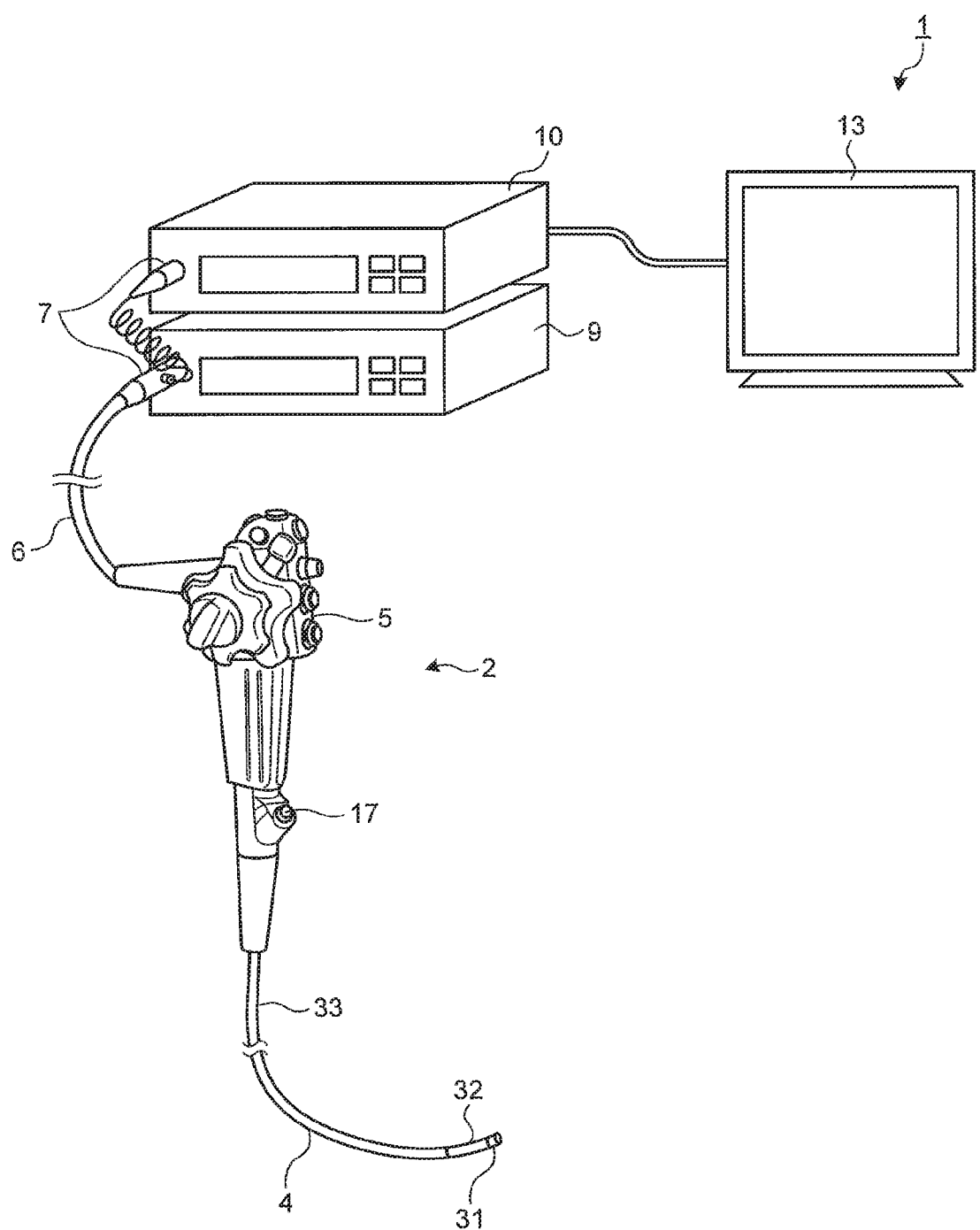
FIG. 1 is a diagram schematically illustrating an entire configuration of an endoscope system according to an embodiment of the present invention.

FIG. 1 is a diagram schematically illustrating an entire configuration of an endoscope system according to the embodiment of the present invention. As illustrated in FIG. 1, an endoscope device 1 includes an endoscope 2, a universal cord 6, a connector 7, a light source device 9, a processor (control device) 10, and a display device 13.

The endoscope 2 captures an in-vivo image of a subject by inserting an insertion portion 4 into a body cavity of the subject and outputs an imaging signal. An electrical cable bundle in the universal cord 6 is extended to a distal end of the insertion portion 4 of the endoscope 2 and connected to an imaging device provided in a distal end portion 31 of the insertion portion 4.

The connector 7 is provided to a proximal end of the universal cord 6, connected to the light source device 9 and the processor 10, applies predetermined signal processing to an imaging signal output from the imaging device in the distal end portion 31 connected with the universal cord 6, and analog-digital converts (A/D converts) the imaging signal to output the imaging signal as an image signal.

The light source device 9 is configured by using, for example, a white LED. Pulse-shaped white light emitted from the light source device 9 becomes irradiation light with which an object is irradiated from the distal end of the insertion portion 4 of the endoscope 2 through the connector 7 and the universal cord 6.

The processor 10 applies predetermined image processing to the image signal output from the connector 7 and controls the entire endoscope device 1. The display device 13 displays the image signal processed by the processor 10.

An operating unit 5 provided with various buttons and knobs for operating endoscope functions is connected to the proximal end of the insertion portion 4 of the endoscope 2. The operating unit 5 is provided with a treatment tool insertion opening 17 from which treatment tools such as an in-vivo forceps, an electrical scalpel, and an inspection probe are inserted into a body cavity of the subject.

The insertion portion 4 includes the distal end portion 31 provided with the imaging device, a bending portion 32 which is bendable in a plurality of directions and is connected to the proximal end of the distal end portion 31, and a flexible tube portion 33 connected to the proximal end of the bending portion 32. A bending tube in the bending portion 32 is bent by an operation of a bending operation knob provided in the operating unit 5 and can be bent in, for example, four directions of up, down, left, and right, following pulling and relaxing actions of a bending wire inserted into the insertion portion 4.

A light guide (not illustrated in the drawings) that transmits illumination light from the light source device 9 is arranged in the endoscope 2 and an illumination lens (not illustrated in the drawings) is arranged at an emitting end of the illumination light transmitted by the light guide. The illumination lens is provided at the distal end portion 31 of the insertion portion 4 and the illumination light with which the subject is irradiated.

Figure 2A:
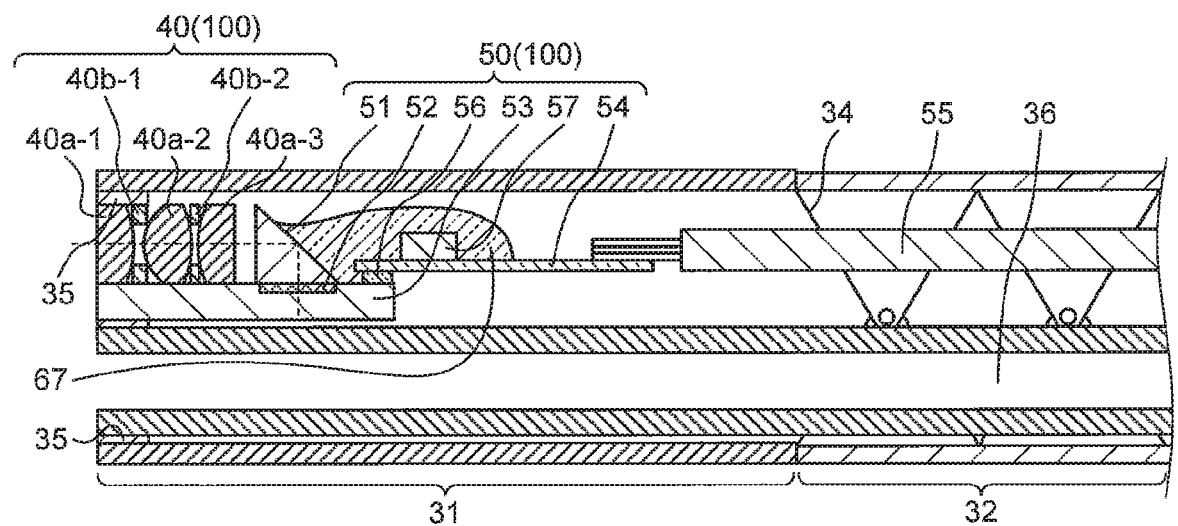
FIG. 2A is a partial cross-sectional view of a distal end of an endoscope illustrated in FIG. 1 in a vertical plane in parallel with an optical axis direction.
Figure 2B:
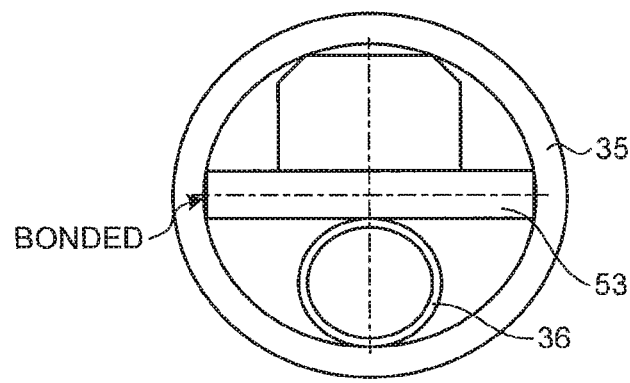
FIG. 2B is a front view of the distal end of the endoscope illustrated in FIG. 1.

Next, a configuration of the distal end portion 31 of the endoscope 2 will be described in detail. FIG. 2A is a cross-sectional view taken along a surface which is orthogonal to a substrate surface of the imaging device provided in the distal end portion 31 of the endoscope 2 and which is in parallel with an optical axis direction of incident light of the imaging device. FIG. 2B is a front view of the distal end portion 31 of the endoscope 2. FIG. 2A illustrates the distal end portion 31 of the insertion portion 4 of the endoscope 2 and a part of the bending portion 32.

As illustrated in FIG. 2A, the bending portion 32 is bendable in four directions of up, down, left, and right following pulling and relaxing actions of a bending wire inserted into a bending tube 34. An imaging device 100 is provided at an upper portion in the distal end portion 31 extended from the distal end of the bending portion 32. A treatment tool channel 36 that causes various treatment tools to extend is formed at a lower portion in the distal end portion 31.

The imaging device 100 includes a lens unit 40 and an imaging unit 50 arranged facing the proximal end of the lens unit 40. The imaging device 100 is bonded to an inner side of the distal end portion 31 with an adhesive. The distal end portion 31 is formed of a rigid member for forming an inner space that houses the imaging device 100. A proximal end outer circumference portion of the distal end portion 31 is covered with a flexible covering tube not illustrated in the drawings. A member located on the proximal end side with respect to the distal end portion 31 is formed of a flexible member so that the bending portion 32 can bend.

The lens unit 40 includes a plurality of objective lenses 40a-1 to 40a-3, spacers 40b-1 and 40b-2 arranged between the objective lenses 40a-1 to 40a-3, and a diaphragm member not illustrated in the drawings. The upper ends of the objective lens 40a-1 and the spacer 40b-1 are inserted and fixed to a distal end fixing portion 35 inside the distal end portion 31, so that the lens unit 40 is fixed to the distal end portion 31. Although the outer diameter of the distal end of the endoscope can be reduced if thickness of an image sensor 53 is reduced, deflective strength significantly decreases because the image sensor 53 is a semiconductor and is made of brittle material such as single-crystal silicon. Therefore, in the embodiment, the image sensor 53 is supported by the distal end fixing portion 35 and the treatment tool channel 36 so that the image sensor 53 can be reinforced so as not to be broken by an external stress and the like. The image sensor 53 may be reinforced by either one of the distal end fixing portion 35 and the treatment tool channel 36 or may be reinforced by another component of the distal end portion 31.

The imaging unit 50 includes a prism 51 that reflects light emitted from the objective lenses 40a-1 to 40a-3 of the lens unit 40 and the image sensor 53 including a light receiving unit 52 that generates an electrical signal by receiving the light reflected by the prism 51 and performing photoelectric conversion. The image sensor 53 is a horizontally placed type where the light receiving unit 52 is horizontally arranged. The prism 51 is bonded onto the light receiving unit 52. A flexible printed circuit board 54 to which a signal cable 55 is connected is connected to the proximal end of the image sensor 53. An electronic component 57 that drives the image sensor 53 is mounted on the flexible printed circuit board 54. The image sensor 53 in the embodiment of the present invention is a charge coupled device (CCD) semiconductor image sensor or a complementary metal oxide semiconductor (CMOS) image sensor.

The proximal end of the signal cable 55 extends in the proximal end direction of the insertion portion 4. The signal cable 55 is inserted and arranged in the insertion portion 4 and extended to the connector 7 through the operating unit 5 and the universal cord 6 illustrated in FIG. 1.

Light that enters the distal end portion 31 is collected by the objective lenses 40a-1 to 40a-3 and enters the prism 51. The light receiving unit 52 receives light emitted from the prism 51 and converts the received light into an imaging signal. The imaging signal is output to the processor 10 through the signal cable 55 connected to the flexible printed circuit board 54 and the connector 7. In the description, a side of the distal end portion 31 through which light enters, that is, a side on which the objective lenses 40a-1 to 40a-3 are arranged, is referred to as a front end portion, and a side on which the prism 51 is arranged is referred to as a rear end portion.

As illustrated in FIG. 2B, side surfaces of the image sensor 53, which are in contact with an inner wall surface of the distal end fixing portion 35, are bonded to the inner wall surface of the distal end fixing portion 35 with an adhesive, and a rear end side of the prism 51 on the image sensor 53 is sealed with a sealing resin 67.

Figure 3A:
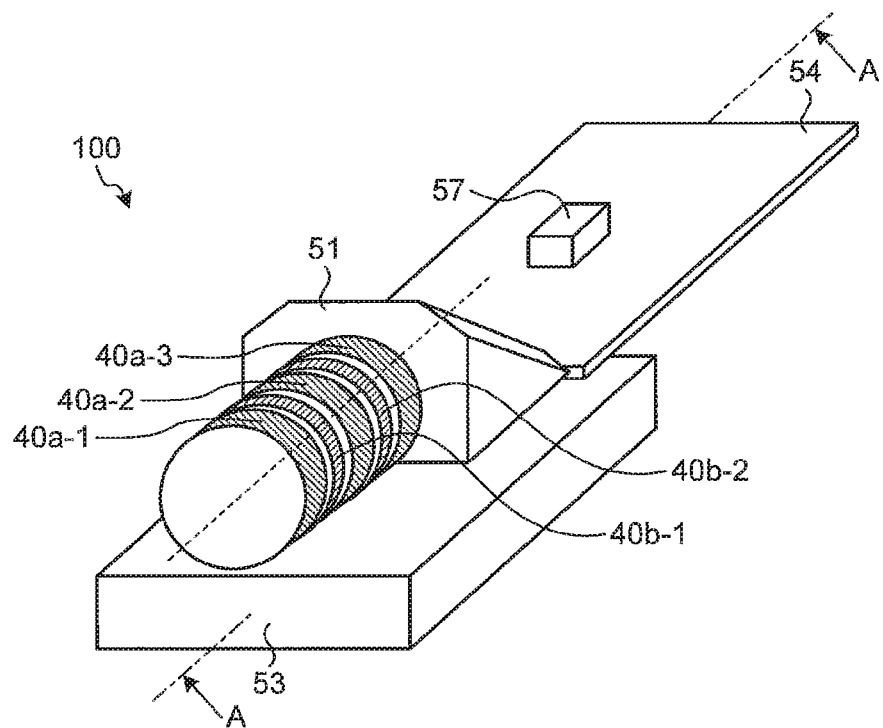
FIG. 3A is a perspective view of an imaging device illustrated in FIG. 2A.
Figure 3B:
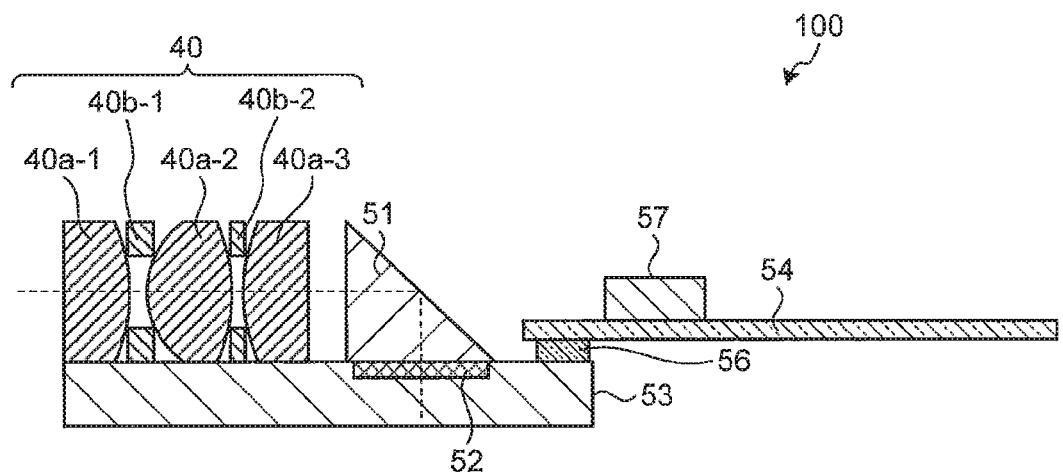
FIG. 3B is a cross-sectional view taken along line A-A in FIG. 3A.

Next, the imaging device 100 according to the embodiment will be described. FIG. 3A is a perspective view of the imaging device 100 illustrated in FIG. 2A. FIG. 3B is a cross-sectional view taken along line A-A in FIG. 3A.

As illustrated in FIGS. 3A and 3B, in the imaging device 100 according to the embodiment, the outer circumferences of the objective lenses 40a-1 to 40a-3 are directly mounted on the surface of the image sensor 53. An imaging optical system is formed by the objective lenses 40a-1 to 40a-3 and the prism 51 and an object image is formed on the light receiving unit 52 of the image sensor 53 by the imaging optical system.

An image sensor electrode 56 connected to the flexible printed circuit board 54 is formed at the rear end portion of the image sensor 53.

In the imaging device 100 according to the embodiment, the gaps between the objective lenses 40a-1 to 40a-3 are adjusted by the spacers 40b-1 and 40b-2 and the positions of the objective lenses 40a-1 to 40a-3 are defined by the spacers 40b-1 and 40b-2. However, the thicknesses of the spacers 40b-1 and 40b-2 in the optical axis direction is smaller than those of the objective lenses 40a-1 to 40a-3, so that it is desirable that each of the spacers 40b-1 and 40b-2 is integrated with any one of the objective lenses 40a-1 to 40a-3. For example, it is desirable that the objective lens 40a-3 and the spacer 40b-2 are integrated together, the objective lens 40a-2 and the spacer 40b-1 are integrated together, and each integrated part is mounted at a predetermined position on the image sensor 53. It is desirable that the diaphragm member not illustrated in the drawings is also integrated with any one of the objective lenses 40a-1 to 40a-3 in the same manner as the spacers 40b-1 and 40b-2. The objective lens and the spacer can be integrated together by moving the objective lens held by a jig on the spacer, performing positioning by image processing, and then bonding the objective lens to the spacer with an adhesive. Alternatively, a metal film as a spacer having a desired thickness may be formed on one surface of an objective lens, and then an optical path of incident light may be formed by etching or the like so that the objective lens and the spacer can be integrated together.

In this way, it is possible to perform so-called passive alignment of the imaging optical system onto the surface of the image sensor 53 by image processing. Further, in order to more accurately align the imaging optical system onto the image sensor 53, it is desirable that the objective lenses 40a-1 to 40a-3, the spacers 40b-1 and 40b-2, and the diaphragm member are integrated with one another to form the lens unit 40 as a single assembled unit, and then so-called active alignment is performed such that the assembled unit is actively aligned by adjusting the position of the assembled unit while checking images output from the image sensor 53.

The lens unit 40 can be integrated as a single assembled unit by coating an adhesive on bonding surfaces of the objective lenses 40a-1 to 40a-3 or the spacers 40b-1 and 40b-2 in advance, dropping, for example, the objective lens 40a-3, the spacer 40b-2, the objective lens 40a-2, the spacer 40b-1, and the objective lens 40a-1 in this order into a frame member for the integration, curing the adhesive, and taking out the lens unit 40 from the frame member.

Figure 4A:
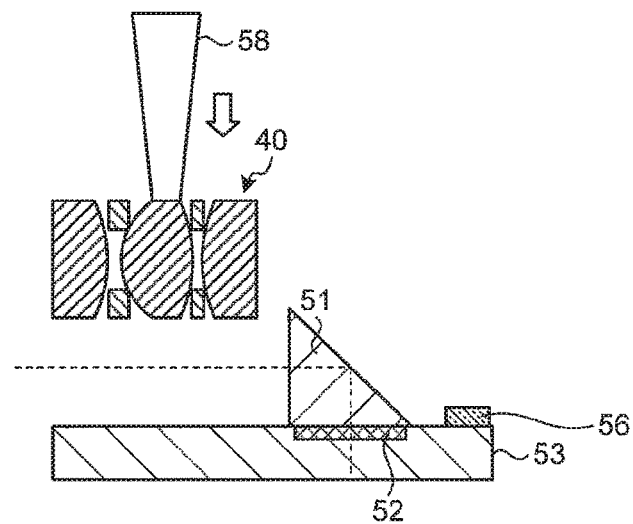
FIGS. 4A and 4B are diagrams for explaining a manufacturing process of the imaging device in FIG. 2A.
Figure 4B:
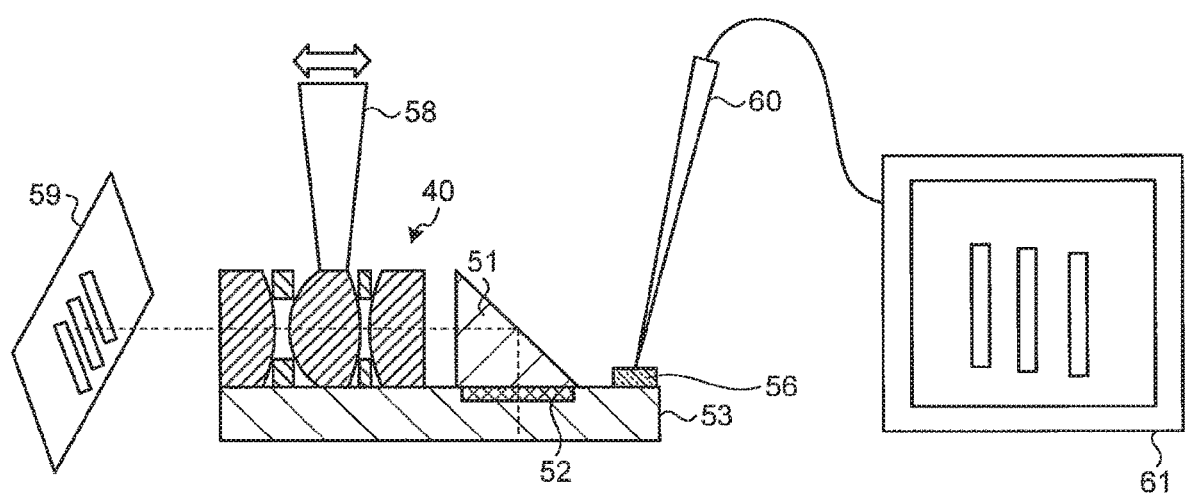

The integrated lens unit 40 is held by a jig 58 having an absorption function and mounted on the image sensor 53 where the prism 51 is connected on the light receiving unit 52 in advance. FIGS. 4A and 4B are diagrams for explaining a manufacturing process of the imaging device 100. As illustrated in FIG. 4A, the integrated lens unit 40 is mounted on the image sensor 53 while the lens unit 40 is held by the jig 58. As illustrated in FIG. 4B, while the lens unit 40 is held by the jig 58, an image of a test chart 59 is captured and the captured image is input into the light receiving unit 52 through the lens unit 40. Image data converted into an electrical signal by the light receiving unit 52 is output to a monitor 61 by contacting a probe 60 to the image sensor electrode 56. The active alignment may be performed by adjusting the position of the lens unit 40 based on the image output to the monitor 61. In the active alignment, the position of the lens unit 40 may be adjusted based on analysis performed by software or the like without outputting the image data to the monitor 61 or the like. The alignment of the lens unit 40 is performed on the image sensor 53, so that it is possible to adjust not only the position of front, rear, left, and right, but also a tilt angle. Therefore, it is possible to accurately define the position.

It is possible to connect the lens unit 40 onto the surface of the image sensor 53 by directly aligning the lens unit 40 onto the image sensor 53 and then curing an adhesive applied in advance to a connection portion between the image sensor 53 and the objective lenses 40a-1 to 40a-3 and the like. In the description, the surface of the image sensor 53 includes not only a surface of silicon that forms a main body of the image sensor 53, but also a thin film surface of pixels and color filters formed on the surface of silicon.

In the imaging device 100 according to the embodiment, it is possible to directly mount the objective lenses 40a-1 to 40a-3 on the image sensor 53 without using a frame member, so that it is possible to achieve a small-sized imaging device 100. Further, the mounting position of the lens unit 40 is defined by the active alignment, so that it is possible to more accurately define the position of the imaging optical system.

Figure 5A:
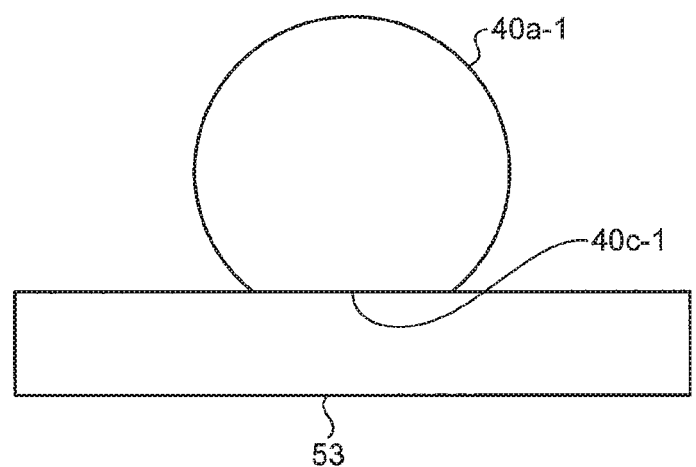
FIG. 5A is a diagram for explaining an imaging device according to a first modified example of the embodiment.

Further, to facilitate the alignment of the objective lenses 40a-1 to 40a-3 to the image sensor 53, flat portions 40c-1 to 40c-3 may be formed on side surfaces of the objective lenses 40a-1 to 40a-3, which are in contact with the image sensor 53. FIG. 5A is a diagram for explaining an imaging device according to a first modified example of the embodiment. The flat portions 40c-1 to 40c-3 (the flat portions 40c-2 and 40c-3 are not illustrated in the drawings) have flat surfaces and can be formed by cutting side surface portions of the objective lenses 40a-1 to 40a-3. When the flat portions 40c-1 to 40c-3 are formed, contact areas between the surface of the image sensor 53 and the objective lenses 40a-1 to 40a-3 increase, so that it is possible to easily and stably define the positions of the objective lenses 40a-1 to 40a-3. The flat portions 40c-1 to 40c-3 are provided, so that even when the objective lenses 40a-1 to 40a-3 and the spacers 40b-1 and 40b-2 are integrated together, it is possible to easily and stably define the position of the lens unit 40.

Figure 5B:
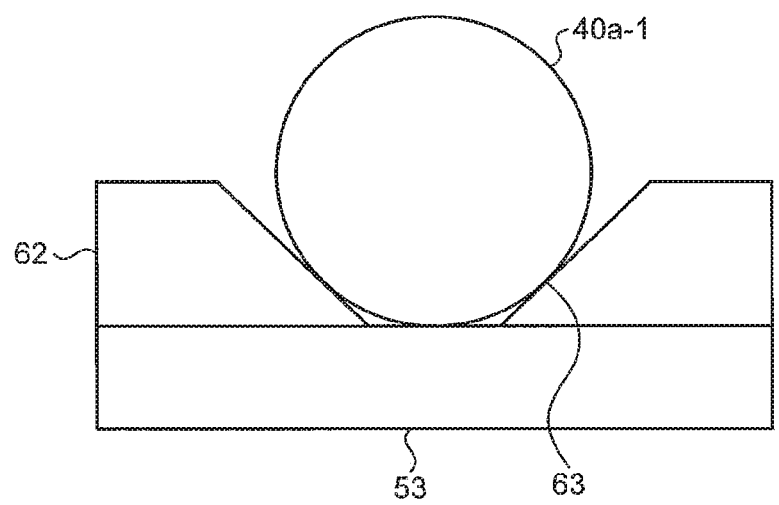
FIG. 5B is a diagram for explaining a lens position defining unit of an imaging device according to a second modified example of the embodiment.

Further, a lens position defining member 62 that defines the positions of the objective lenses 40a-1 to 40a-3 may be provided on the image sensor 53. FIG. 5B is a diagram for explaining an imaging device according to a second modified example of the embodiment. The lens position defining member 62 is formed of a silicon block and has a groove portion 63 having a V shape in a vertical cross section. In the lens position defining member 62, the groove portion 63 having the V shape can be formed by bonding a plate-shaped silicon block onto the surface of the image sensor 53 and etching the bonded silicon block. Regarding the lens position defining member 62, a lens position defining member having a length greater than or equal to the length of the lens unit 40 including the spacers 40b-1 and 40b-2 in the optical axis direction may be formed and the position of the integrated lens unit 40 may be defined by the lens position defining member 62. Alternatively, a plurality of lens position defining members corresponding to the objective lenses 40*a*-1 to 40*a*-3 may be formed at positions where the objective lenses 40*a*-1 to 40*a*-3 are mounted and the position may be defined for each of the objective lenses 40*a*-1 to 40*a*-3.

Figure 5C:
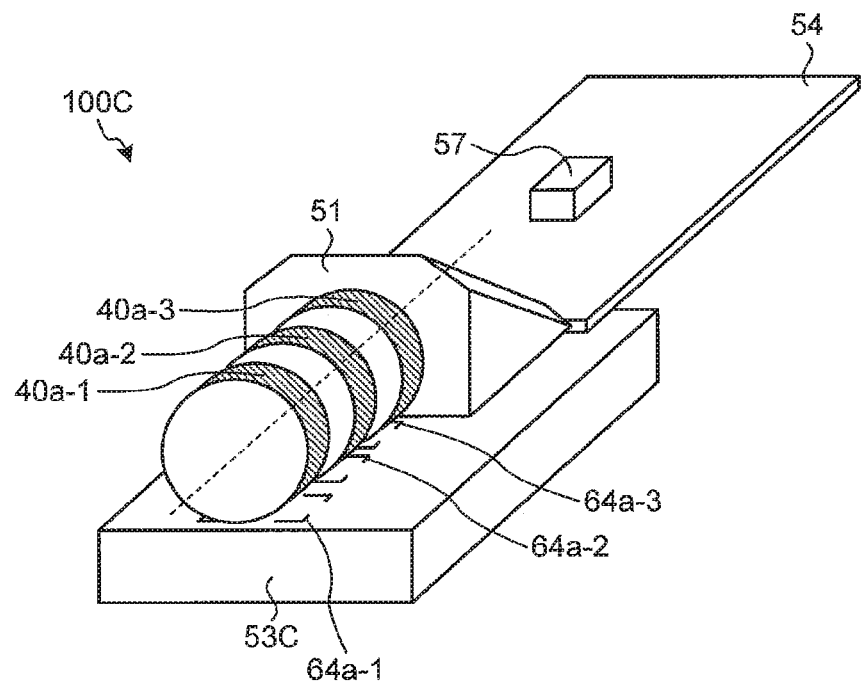
FIG. 5C is a perspective view for explaining a lens position defining unit of an imaging device according to a third modified example of the embodiment.

Furthermore, a lens position defining unit formed on the image sensor may be alignment marks. FIG. 5C is a perspective view for explaining an imaging device 100C according to a third modified example of the embodiment. Alignment marks 64*a*-1 to 64*a*-3 are formed on an image sensor 53C by photolithography or the like and are provided so as to correspond to connection positions of the objective lenses 40*a*-1 to 40*a*-3. The objective lenses 40*a*-1 to 40*a*-3 are moved to the corresponding alignment marks 64*a*-1 to 64*a*-3 while an upper surface of each of the objective lenses 40*a*-1 to 40*a*-3 is sucked by a jig or the like, and are fixed onto the image sensor 53C after position adjustment is passively performed while checking the positions of the objective lenses 40*a*-1 to 40*a*-3 and the alignment marks 64*a*-1 to 64*a*-3 as the lens position defining unit, by a camera or the like from above. The objective lenses 40*a*-1 to 40*a*-3 used in the third modified example may have the flat portions 40*c*-1 to 40*c*-3, respectively.

Figure 5D:
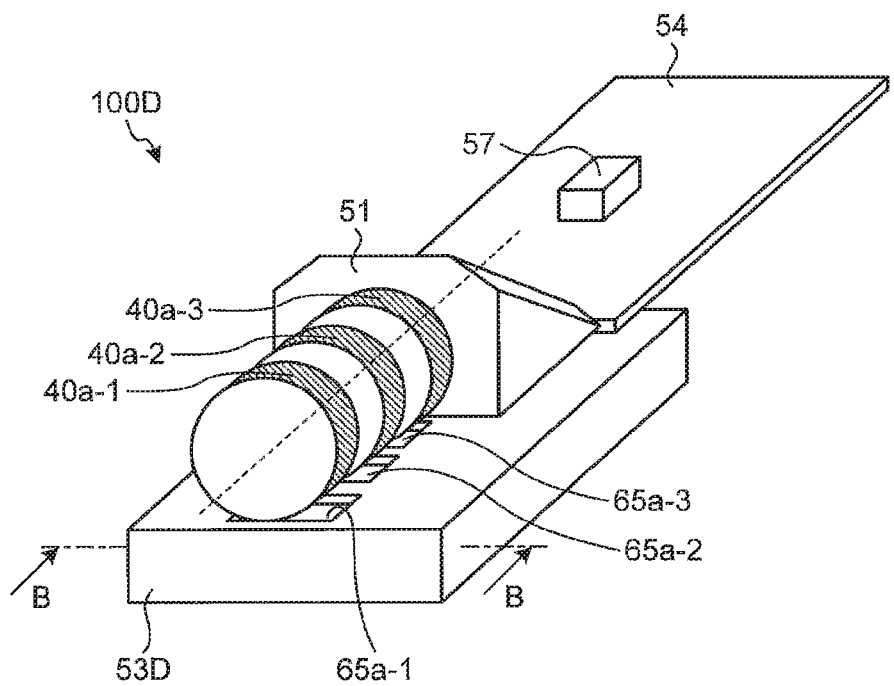
FIG. 5D is a perspective view for explaining a lens position defining unit of an imaging device according to a fourth modified example of the embodiment.
Figure 5E:
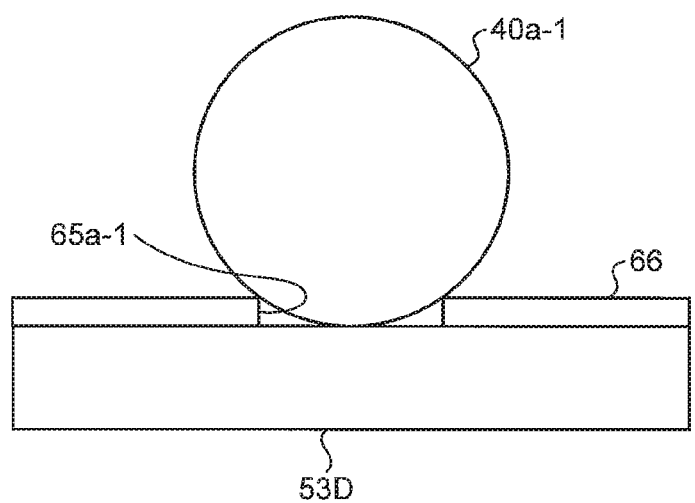
FIG. 5E is a cross-sectional view taken along line B-B in FIG. 5D.

Further, the lens position defining unit formed on the image sensor may be recessed portions formed on a thin film such as a color filter formed on the surface of the image sensor. FIG. 5D is a perspective view for explaining a lens position defining unit of an imaging device 100D according to a fourth modified example of the embodiment. FIG. 5E is a cross-sectional view taken along line B-B in FIG. 5D.

Recessed portions 65*a*-1 to 65*a*-3 are formed by etching a thin film 66. In general, the thickness of the thin film 66 such as a color filter formed on the surface of the image sensor 53D is about 10 μm. The recessed portions 65*a*-1 to 65*a*-3 are formed by removing parts of the thin film 66 at connection positions of the objective lenses 40*a*-1 to 40*a*-3. Even when the depth of the recessed portions is about the thickness of the thin film 66, as illustrated in FIG. 5E, the positions of the objective lenses 40*a*-1 to 40*a*-3 can be passively defined by fitting the objective lenses 40*a*-1 to 40*a*-3 into the recessed portions 65*a*-1 to 65*a*-3.

In the third and fourth modified examples, the front end surface of the objective lens 40*a*-1 is located behind the front end side surface of the image sensor. However, it is preferable that the objective lens 40*a*-1 is mounted at a position where the surface of the connected image sensor is out of the viewing angle. In the other examples, the front end surface of the objective lens 40*a*-1 is matched to the front end side surface of the image sensor. However, if the front end surface of the objective lens 40*a*-1 is arranged in front of the front end side surface of the image sensor, when the objective lens 40*a*-1 is inserted into the distal end portion of the endoscope device or the like and inserted and fixed to the distal end fixing portion, inside liquid tightness is easily maintained.

According to some embodiments, a lens group is directly mounted on a surface of an image sensor. With this structure, it is possible to reduce a diameter and length of an imaging device.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging device comprising:
   a lens group comprising at least a plurality of lenses configured to collect incident light;
   a prism configured to reflect the light collected by the lens group; and
   an image sensor having a light receiving unit configured to receive the light reflected by the prism, the light receiving unit being configured to perform photoelectric conversion on the received light to generate an electrical signal,
   wherein the prism is mounted on the light receiving unit, and
   a circumferential surface of at least one of the plurality of lenses of the lens group is directly fixed by an adhesive on a same surface on which the light receiving unit of the image sensor is arranged.

2. The imaging device according to claim 1, wherein the circumferential surface comprises a flat portion on a bottom surface of the lens group that is in contact with the image sensor.

3. The imaging device according to claim 1, further comprising a lens position defining unit arranged on the same surface on which the light receiving unit of the image sensor is arranged to define a position of the lens group.

4. The imaging device according to claim 3, wherein the lens position defining unit comprises a silicon block whose vertical cross section has a V shape.

5. The imaging device according to claim 3, wherein the lens position defining unit comprises a recessed portion on a thin film formed on the same surface on which the light receiving unit of the image sensor is arranged.

6. The imaging device according to claim 3, wherein the lens position defining unit comprises an alignment mark formed on the same surface on which the light receiving unit of the image sensor is arranged.

7. The imaging device according to claim 1, wherein
   the lens group is an assembled unit in which at least a plurality of objective lenses and a plurality of spacers arranged between the plurality of objective lenses are integrated with one another, and
   when a position of the assembled unit is defined on the image sensor, the position of mounting the assembled unit is adjusted based on image information input from the assembled unit.

8. The imaging device according to claim 1, wherein
   the lens group includes at least a plurality of objective lenses and a plurality of spacers arranged between the plurality of objective lenses, and
   at least the plurality of objective lenses and the plurality of spacers are directly mounted on the same surface on which the light receiving unit of the image sensor is arranged.

9. An endoscope device configured to be inserted into a living body, the endoscope device comprising the imaging device according to claim 1 to image an inside of the living body.

10. The imaging device according to claim 1, wherein at least the plurality of lenses being fixed together into the lens group and the circumferential surface of the at least one of the plurality of lenses of the lens group is directly fixed on the same surface on which the light receiving unit of the image sensor is arranged.

11. The imaging device according to claim 10, wherein at least the plurality of lenses being fixed together into the lens group by an adhesive.

\* \* \* \* \*